United States Patent
Gerspacher et al.

(10) Patent No.: US 6,319,917 B1
(45) Date of Patent: Nov. 20, 2001

(54) ACYLAMINOALKENYLENE-AMIDE DERIVATIVES AS NK1 AND NK2 ANTAGONISTS

(75) Inventors: Marc Gerspacher, Gipf-Oberfrick; Andreas von Sprecher, Oberwil; Robert Mah, Allschwil; Silvio Roggo, Muttenz; Stefan Stutz, Basel, all of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/655,170

(22) Filed: Sep. 5, 2000

Related U.S. Application Data

(63) Continuation of application No. 09/242,594, filed as application No. PCT/EP97/04436 on Aug. 13, 1997.

(30) Foreign Application Priority Data

Aug. 22, 1996 (CH) .................................................. 2061/96

(51) Int. Cl.[7] .......................... A61K 31/55; C07D 403/12
(52) U.S. Cl. ........................... 514/212; 540/524; 548/495; 564/152
(58) Field of Search ........................... 564/152; 548/495; 540/524; 514/212

(56) References Cited

U.S. PATENT DOCUMENTS

| | | |
|---|---|---|
| 5,217,996 | 6/1993 | Ksander ................ 514/533 |
| 5,929,067 | 7/1999 | Gerspacher et al. ............. 514/212 |

FOREIGN PATENT DOCUMENTS

| | | |
|---|---|---|
| 0 532 456 A1 | 3/1993 | (EP) . |
| 0 716 077 A | 6/1996 | (EP) . |
| 93/01169 | 1/1993 | (WO) . |
| 96 26183A | 8/1996 | (WO) . |

OTHER PUBLICATIONS

Angus M. MacLeod, et al., J. Med. Chem. vol. 36, 1993, pp. 2044–2045.

Cs. Somlai and L. Balaspiri, J. Prakt. Chem., vol. 336, 1994, pp. 525–529.

S. Natarajan, et al., "Nonhydrolyzable Tripeptide Analogs as Angiotensin–Converting Enzyme Inhibitors", The Squibb Institute for Medical Research, Princeton, NJ, pp. 429–433.

*Primary Examiner*—Robert Gerstl
(74) *Attorney, Agent, or Firm*—Carol A. Loeschorn

(57) ABSTRACT

Compounds of formula I

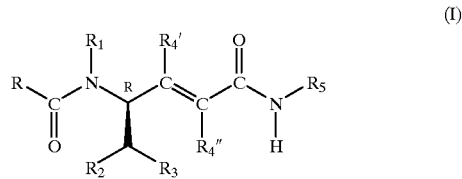

(I)

wherein $R_1$, $R_1$–$R_3$, $R_4'$, $R_4''$ and $R_5$ are as defined in the description, have valuable pharmaceutical properties and are effective especially as NK1 and NK2 antagonists. They are prepared in a manner known per se.

14 Claims, No Drawings

ACYLAMINOALKENYLENE-AMIDE DERIVATIVES AS NK1 AND NK2 ANTAGONISTS

This is a continuation of Ser. No. 09/242,594, Sep. 30, 1999, pending, which is a 371 of PCT/EP97/04436, Aug. 13, 1997.

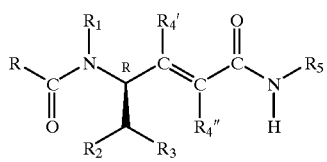

(I)

The invention relates to the compounds of formula I wherein

R is phenyl that is unsubstituted or is substituted by 1, 2 or 3 substituents selected from the group halogen, lower alkyl, trifluoromethyl, hydroxy and lower alkoxy, $R_1$ is hydrogen or lower alkyl, $R_2$ is hydrogen, lower alkyl or phenyl that is unsubstituted or is substituted by 1, 2 or 3 substituents selected from the group halogen, lower alkyl, trifluoromethyl, hydroxy and lower alkoxy, $R_3$ is phenyl that is unsubstituted or is substituted by 1, 2 or 3 substituents selected from the group halogen, lower alkyl, trifluoromethyl, hydroxy and lower alkoxy; or is naphthyl, 1H-indol-3-yl or 1-lower alkyl-indol-3-yl, $R_4'$ and $R_4''$ are each independently of the other hydrogen or lower alkyl, at least one of the radicals $R_4'$ and $R_4''$ being hydrogen, and $R_5$ is $C_3$–$C_8$cycloalkyl, D-azacycloheptan-2-on-3-yl or L-azacycloheptan-2-on-3-yl; and salts thereof, to processes for the preparation of those compounds, to pharmaceutical compositions comprising those compounds, to the use of those compounds in the therapeutic treatment of the human or animal body or in the manufacture of pharmaceutical compositions.

The general terms used hereinabove and hereinbelow preferably have the following meanings within the scope of this Application:

The term "lower" denotes a radical having up to and including 7 and especially up to and including 4 carbon atoms.

Lower alkyl is, for example, $C_1$–$C_7$alkyl, preferably $C_1$–$C_4$alkyl, especially methyl and ethyl, and more especially methyl. Examples of lower alkyl are methyl, ethyl, n-propyl, isopropyl, n-butyl, isobutyl, sec-butyl, tert-butyl, n-pentyl, neopentyl, n-hexyl and n-heptyl.

Halogen is, for example, fluorine, chlorine, bromine or iodine.

Halophenyl is, for example, (fluoro-, chloro-, bromo- or iodo-)phenyl, preferably fluorophenyl or chlorophenyl, especially 4-fluorophenyl or 4-chlorophenyl, and more especially 4-chlorophenyl.

Dihalophenyl is, for example, dichlorophenyl, difluorophenyl or chlorofluorophenyl, preferably dichlorophenyl or difluorophenyl, especially 3,4-dichlorophenyl or 3,4-difluorophenyl, and more especially 3,4-dichlorophenyl.

Trihalophenyl is, for example, trifluorophenyl or trichlorophenyl.

1-Lower alkyl-indol-3-yl is, for example, 1-methyl-indol-3-yl.

$C_3$–$C_8$Cycloalkyl—and analogously $C_5$–$C_7$cycloalkyl—is in each case a cycloalkyl radical having the number of ring carbon atoms indicated. $C_3$–$C_8$Cycloalkyl is therefore, for example, cyclopropyl, cyclobutyl, cyclopentyl, cyclohexyl, cycloheptyl or cyclooctyl, preferably cyclohexyl.

D-Azacycloheptan-2-on-3-yl corresponds to the following group

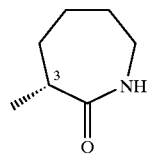

which is derived from D(+)-epsilon-caprolactam (amino-) substituted in the 3-position [≈D-3-amino-epsilon-caprolactam=(R)-3-amino-hexahydro-2-azepinone]. Analogously, L-aza-cycloheptan-2-on-3-yl corresponds to the group

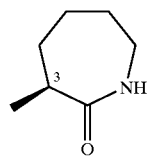

which is derived from L(−)-epsilon-caprolactam (amino-) substituted in the 3-position [≈L-3-amino-epsilon-caprolactam=(S)-3-amino-hexahydro-2-azepinone].

Salts of compounds of formula I are especially pharmaceutically acceptable salts. Compounds of formula I having a basic group may, for example, form acid addition salts with suitable mineral acids, such as hydrohalic acids, sulfuric acid or phosphoric acid, for example hydrochlorides, hydrobromides, sulfates, hydrogen sulfates or phosphates.

Where the compounds of formula I contain an acid group, corresponding salts with bases are also possible, for example corresponding alkali metal or alkaline earth metal salts, for example sodium, potassium or magnesium salts, or salts with ammonia or organic amines, for example ammonium salts.

The compounds of formula I have valuable pharmacological properties. In particular, they act as neurokinin antagonists (NK antagonists) and are therefore capable of preventing disease symptoms that are caused inter alia by the production of substance P (NK1 receptor) and neurokinin A [=NKA] (NK2 receptor).

The respiratory tract is equipped with sensory nerves that contain a number of neuropeptides, especially tachykinins and CGRP (=calcitonin gene-related peptide). The activation of the sensory nerves results in a local release of neuropeptides inside the lungs. More especially substance P and neurokinin A are produced, which trigger an acute inflammatory reaction termed neurogenic inflammation. That inflammatory reaction proceeds mainly via NK1 receptor activation and includes especially vasodilatation, microvascular leakage, recruitment of inflammatory leukocytes and excessive secretion of mucus, and also bronchoconstriction [mainly via activation of the neurokinin 2 receptor (NK2 receptor)]. Those tachykinin effects are typical features of asthma.

The pharmacological action of the compounds of formula I is based especially on the antagonisation of the NK1 receptor and additionally generally also on the antagonisation of the NK2 receptor. The compounds of formula I are therefore capable of inhibiting neurogenic inflammation and tachykinin-induced bronchoconstriction.

The advantageous effects of the compounds of formula I can be demonstrated by various in vitro or in vivo test methods. For example, in vitro they inhibit the [beta-Ala8] NKA(4–10)-induced $Ca^{2+}$ influx into ovarian cells of transfected Chinese hamsters, which express recombinant human neurokinin 2 receptors, with $IC_{50}$ values from about 10 nM. Furthermore, in an NK-2 binding assay, in which they are tested for their ability to inhibit the binding of $^{125}$I-NKA to hrNK2CHO cells [culture conditions and cell isolation for hrNK2CHO cells, see N. Subramanian et al., Biochem. Biophys. Req. Comm. 200 (1994) 1512–1520], they exhibit $IC_{50}$ values from about 1 nM. In addition, they are effective, for example, in vivo in the NK1 bronchospasm test in guinea pigs with $ED_{50}$ values of about 0.05–1 mg/kg p.o., the test compounds being given 2, 4, 12 or 24 hours prior to the intravenous administration of 3.0 µg/kg of [Sar9,Met(O2) 11]-substance P[=SarSP]. The challenge by SarSP induces an increase in intratracheal pressure in the guinea pigs. Furthermore, some of the compounds of formula I are effective p.o. also in the in vivo NK2 bronchospasm test in guinea pigs. In that case the increase in intratracheal pressure is induced by intravenous administration of 0.8 µg/kg of [beta-Ala8]NKA(4–10), the test compounds being administered, for example, 2 hours prior to the challenge.

The compounds of formula I are effective especially as antagonists of NK1 receptors. Their action on that class of receptors and their action on related receptor systems, for example NK2, render the compounds of formula I therapeutically useful in the prevention, the treatment or the diagnosis of a number of diseases, for example diseases of the upper and lower respiratory tract, for example bronchial asthma, allergic asthma, non-allergic asthma, allergic hypersensitivity and hypersecretion conditions, such as chronic bronchitis and cystic fibrosis; pulmonary fibrosis of various aetiologies; diseases of the pulmonary and bronchial circulation, such as pulmonary high blood pressure, angiogenesis, metastases; diseases of the gastrointestinal tract, such as Crohn's disease, Hirsprung's disease, diarrhoea, mal-absorption conditions, inflammatory conditions; in affective, traumatic or inflammatory disorders of the central and peripheral nervous system, such as depression, anxiety states, migraine and other forms of cranial pain, strokes, emesis; diseases of the blood vessels, such as the cranial vessels; diseases relating to the microcirculation in various tissues, such as the skin and eyes; diseases of the immune system and of the reticulohistiocytary system, such as in the splenic and lymphatic tissues; conditions of pain and other disorders in which the action of neurokinins, tachykinins or other related substances are involved in the pathogenesis, pathology and aetiology.

As already mentioned, the compounds of formula I act as antagonists of substance P. Substance P plays an important role in various disorders, for example in conditions of pain, in migraine and in certain disorders of the central nervous system, such as in anxiety states, emesis, schizophrenia and depression, and in certain motor disorders, such as in Parkinson's disease, and also in inflammatory diseases, such as in rheumatoid arthritis, iritis and conjunctivitis, in diseases of the respiratory organs, such as in asthma and chronic bronchitis, in disorders of the gastrointestinal system, such as in ulcerative colitis and Crohn's disease, and in hypertension.

The substance-P-antagonising effects can be demonstrated, for example, as follows: in vitro, for example, the binding of $^3$H-substance P to the bovine retina in the radio receptor assay according to H. Bittiger, Ciba Foundation Symposium 91 (1982)196–199, is inhibited with $IC_{50}$ values of from about 0.2 nM.

The invention relates preferably to the compounds of formula I wherein

R is phenyl, 3,5-bistrifluoromethyl-phenyl or 3,4,5-trimethoxyphenyl, $R_1$ is hydrogen or lower alkyl, $R_2$ is hydrogen or phenyl, $R_3$ is phenyl, halo-phenyl, dihalo-phenyl, trihalo-phenyl, 2-naphthyl, 1H-indol-3-yl or 1-lower alkyl-indol-3-yl, $R_4'$ and $R_4''$ are each independently of the other hydrogen or lower alkyl, at least one of the radicals $R_4'$ and $R_4''$ being hydrogen, and $R_5$ is $C_5$–$C_7$cycloalkyl, D-azacycloheptan-2-on-3-yl or L-azacycloheptan-2-on-3-yl; and salts thereof.

The invention relates especially to compounds of formula I wherein

R is 3,5-bistrifluoromethyl-phenyl, $R_1$ is hydrogen, methyl or ethyl, $R_2$ is hydrogen or phenyl, $R_3$ is phenyl, 4-chlorophenyl, 4-fluorophenyl, 3,4-dichloro-phenyl, 3,4-difluoro-phenyl, 3-fluoro-4-chloro-phenyl, 3,4,5-trifluoro-phenyl, 2-naphthyl, 1 H-indol-3-yl or 1-methyl-indol-3-yl, $R_4'$ and $R_4''$ are each independently of the other hydrogen or methyl, at least one of the radicals $R_4'$ and $R_4''$ being hydrogen, and $R_5$ is cyclohexyl, D-azacycloheptan-2-on-3-yl or L-azacycloheptan-2-on-3-yl; and pharmaceutically acceptable salts thereof.

The invention relates more especially to compounds of formula I wherein

R is 3,5-bistrifluoromethyl-phenyl, $R_1$ is hydrogen or methyl, $R_2$ is hydrogen or phenyl, $R_3$ is phenyl, 4-chlorophenyl, 3,4-dichloro-phenyl, 2-naphthyl, 1 H-indol-3-yl or 1-methyl-indol-3-yl, $R_4'$ and $R_4''$ are hydrogen, and $R_5$ is cyclohexyl, D-azacycloheptan-2-on-3-yl or L-azacycloheptan-2-on-3-yl; and pharmaceutically acceptable salts thereof.

Special mention should be made of each of the following sub-groups of a group of compounds of formula I:

(1) compounds of formula I wherein $R_5$ is D-azacycloheptan-2-on-3-yl; (2) compounds of formula I wherein $R_4'$ and $R_4''$ are hydrogen; (3) compounds of formula I wherein R is phenyl, 3,5-bistrifluoromethyl-phenyl or 3,4,5-trimethoxyphenyl; (4) compounds of formula I in free form, that is to say not in the form of a salt.

The invention relates especially to the specific compounds described in the Examples.

The compounds of formula I can be prepared in a manner known per se, for example by (A) N-acylating a compound of formula II

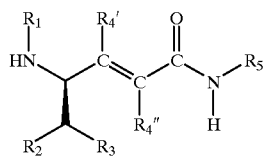
(II)

with a carboxylic acid R—C(=O)—OH, or with a reactive derivative thereof, or
(B) condensing a carboxylic acid of formula III

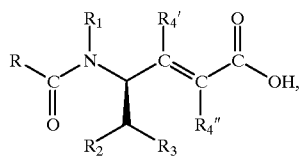
(III)

or a reactive derivative thereof, with a $C_3$–$C_8$cycloalkyl-amine or D(+)- or L(-)-3-amino-epsilon-caprolactam, or
(C) as a last step, synthesising the double bond by a Wittig reaction or a variant thereof, for example Wittig-Horner; and, if desired, converting a compound of formula I into a different compound of formula I and/or, if desired, converting a resulting salt into the free compound or into a different salt and/or, if desired, converting a resulting free compound of formula I having salt-forming properties into a salt and/or, if desired, separating a resulting mixture of stereoisomers, diastereoisomers or enantiomers into the individual stereoisomers, diastereoisomers or enantiomers.

In the following more detailed description of the processes, unless otherwise indicated the symbols R, $R_1$–$R_3$, $R_4'$, $R_4''$ and $R_5$ are each as defined for formula I.

Process (A): The reaction according to Process (A) corresponds to the N-acylation known per se of primary and secondary amines, that is to say the formation of arylcarboxylic acid amides from the corresponding carboxylic acids, or derivatives thereof, and primary and secondary amines. One of the numerous possible methods that may be mentioned is the N-acylation of a compound of formula II with a carboxylic acid chloride $R_1$—COCl, e.g. 3,5-bis-trifluoromethyl-benzoic acid chloride, for example in the presence of triethylamine and optionally 4-dimethylaminopyridine (DMAP).

The compounds of formula II are prepared, for example, as follows: the starting material used is a compound of formula IV

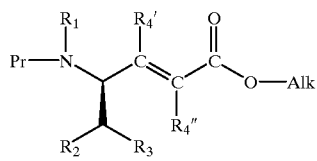
(IV)

wherein Pr is an amino-protecting group [for example BOC=tert-butyloxycarbonyl (—COO—tert-butyl)] and Alk is $C_1$–$C_7$alkyl. The alkyl ester is hydrolysed to the carboxylic acid, the radical —$NHR_5$ is introduced by reaction with the corresponding amine $H_2NR_5$ [formation of —C(=O)—$NHR_5$] and finally the protecting group -Pr is removed.

A compound of formula IV can be obtained, for example, by using as starting material an alpha-amino acid derivative of formula V

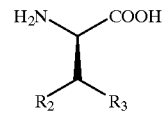
(V)

(e.g. $R_2$=H, $R_3$=phenyl, D-phenylalanine), protecting the free amino group with a protecting group "Pr" [e.g. BOC by reaction with $(BOC)_2O$], optionally introducing the group $R_1$, for example by N-alkylation, and esterifying the carboxylic acid radical (preferably to form a lower alkyl ester, especially the methyl ester). If desired, the introduction of the group $R_1$ and the esterification of the carboxylic acid radical can be carried out also in one step, for example with methyl iodide and $Ag_2O$ in DMF. The carboxylic acid ester is reduced to the corresponding aldehyde Va

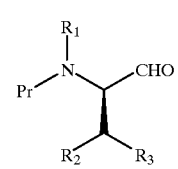
(Va)

(e.g. with diisobutylaluminium hydride in toluene at $-78°$ C.) and finally reacted to form the compound of formula IV in a Wittig-Horner reaction. That can be effected, for example, by reaction with a phosphonoalkanoic acid trialkyl ester of the formula $(AlkO)_2P(=O)$—$CH_2$—COOAlk (Alk=$C_1$–$C_7$alkyl).

In an advantageous variant of the preparation of compounds of formula IV described above, the known esters of formula Vb (with Alk=lower alkyl, especially methyl)

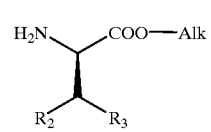
(Vb)

are used as starting material (instead of the carboxylic acids of formula V) and then a procedure analogous to that described above is carried out, that is to say the free amino group is again protected by a protecting group "Pr", optionally the group $R_1$ is introduced and the compound is reduced to the aldehyde Va.

If the aldehyde Va is reacted in the Wittig-Horner reaction with a phosphonoalkanoic acid trialkyl ester of the formula $(AlkO)_2P(=O)$—CH(—Alk)—COOAlk (Alk=$C_1$–$C_7$alkyl), then compounds of formula IV wherein $R_4''$ is lower alkyl are obtained.

If compounds of formula IV wherein $R_4'$ is lower alkyl are to be prepared, then, for example, an aldehyde of formula Va can be reacted with a lower alkyl-magnesium halide, for example methyl-magnesium iodide, to form a secondary alcohol which can then be converted, for example by Swern oxidation (oxalyl chloride, DMSO), into a ketone of formula Vc

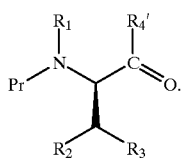
(Vc)

The latter is then reacted analogously to the aldehyde Va in a Wittig-Horner reaction to form a compound of formula IV (wherein $R_4'$=lower alkyl).

Process (B): The reaction according to Process (B) corresponds to the formation known per se of carboxylic acid amides from the corresponding carboxylic acids, or reactive derivatives thereof, and primary amines. Of the large number of possible methods the following may be mentioned: (1) the reaction of a carboxylic acid of formula III with a primary amine $H_2NR_5$, for example in the presence of N-ethyl-N'-(3-dimethylaminopropyl)-carbodiimide hydrochloride (EDC) and 4-dimethylaminopyridine (DMAP); (2) the reaction of a carboxylic acid of formula III first with N-hydroxysuccinimide and N-ethyl-N'-(3-dimethylaminopropyl)-carbodiimide hydrochloride in the presence of DMAP to form the corresponding N-hydroxysuccinimide ester and then with the corresponding amine $H_2NR_5$; (3) the reaction of a carboxylic acid of formula III with an amine $H_2NR_5$ in the presence of 1-propanephosphonic acid anhydride.

The compounds of formula III are prepared, for example, as follows: starting from a compound of formula IV, the amino-protecting group is removed, for example in the case of BOC by reaction with trifluoroacetic acid, the amino group is acylated with a carboxylic acid R-COOH (e.g. 3,5-bistrifluoromethyl-benzoic acid), or with a reactive derivative thereof, [analogously to Process (A)], and finally the alkyl ester group is hydrolysed, for example with LiOH in methanol and THF.

Process (C): A possible starting compound for the Wittig-(Horner) reaction is, for example, an aldehyde of formula Va in which the amino-protecting group is removed and which is then N-acylated with a carboxylic acid R-COOH (e.g. 3,5-bistrifluoromethyl-benzoic acid), or with a reactive derivative thereof, [analogously to Process (A)]. Such an aldehyde can, for example, be reacted with a phosphonoalkanoic acid dialkyl ester amide of the formula $(AlkO)_2P(=O)$—CO—$NHR_5$ in a Wittig-Horner reaction to form a compound of formula I.

Compounds of formula I can also be converted in a manner known per se into other compounds of formula I.

For example, compounds of formula I wherein $R_1$ is lower alkyl can be obtained by N-alkylating a compound of formula I wherein $R_1$ is hydrogen with a compound $Y_3$–$R_1$ wherein $Y_3$ is hydroxy or reactive esterified hydroxy. Reactive esterified hydroxy is, for example, halogen, especially bromine, iodine or chlorine, or sulfonyloxy, for example methylsulfonyloxy or p-toluenesulfonyloxy. Another possible method consists of reacting a compound of formula I wherein $R_1$ is hydrogen with a compound $Y_4$–$R_1'$ wherein $Y_4$ is formyl and $R_1'$ is a radical $R_1$ minus a $CH_2$ group [$R_1$=—$CH_2$–$R_1'$], under reductive conditions (reductive amination).

If any intermediates contain interfering reactive groups, for example carboxy, hydroxy, mercapto or amino groups, those groups can temporarily be protected by readily removable protecting groups. The choice of suitable protecting groups and the manner in which they are introduced and removed are known per se and are described, for example, in J. F. W. McOmie, Protective Groups in Organic Chemistry, Plenum Press, London, N.Y. 1973.

Salts of compounds I can be prepared in a manner known per se. For example, acid addition salts of compounds I are obtained by treatment with a suitable acid or with a suitable ion exchange reagent, and salts with bases are obtained by treatment with a suitable base or with a suitable ion exchange reagent. Salts of compounds of formula I can be converted into the free compounds I in customary manner: acid addition salts, for example, by treatment with a suitable basic agent or with a suitable ion exchange reagent, and salts with bases, for example, by treatment with a suitable acid or with a suitable ion exchange reagent.

The compounds of formula I, including their salts (of salt-forming compounds of formula I), may also be obtained in the form of their hydrates and/or may include other solvents, for example solvents which may have been used for the crystallisation of compounds in solid form.

Depending upon the nature of the variables and the corresponding number of centres of asymmetry and also upon the starting materials and procedures chosen, the compounds of formula I may be obtained in the form of mixtures of stereoisomers, for example mixtures of diastereoisomers or mixtures of enantiomers, such as racemates, or possibly also in the form of pure stereoisomers. Mixtures of diastereoisomers obtainable in accordance with the process or by some other method can be separated in customary manner into mixtures of enantiomers, for example racemates, or into individual diastereoisomers, for example on the basis of the physico-chemical differences between the constituents in known manner by fractional crystallisation, distillation and/or chromatography. Advantageously the more active isomer is isolated.

Mixtures of enantiomers, especially racemates, obtainable in accordance with the process or by some other method can be separated into the individual enantiomers by known methods for example by recrystallisation from an optically active solvent, with the aid of microorganisms, by chromatography and/or by reaction with an optically active auxiliary compound, for example a base, acid or alcohol, to form mixtures of diastereoisomeric salts or functional derivatives, such as esters, separation thereof and freeing of the desired enantiomer. Advantageously the more active enantiomer is isolated.

The invention relates also to those forms of the process according to which a compound obtainable as intermediate at any stage of the process is used as starting material and the remaining steps are carried out or a starting material is used in the form of a derivative or salt or, especially, is formed under the reaction conditions. The invention relates also to the end products having the (4S)-configuration described in the following Examples, which likewise have a certain action as NK1/NK2 antagonists.

In the process of the present invention it is preferable to use those starting materials and intermediates, in each case in free form or in salt form, which result in the compounds I, or their salts, described at the beginning as being especially valuable. The invention relates also to novel starting materials and intermediates, in each case in free form or in salt form, for the preparation of the compounds I or their salts, to their use and to processes for their preparation, the variable R being as defined for the compounds I.

The invention relates also to the use of the compounds I and their pharmaceutically acceptable salts in the treatment of allergic conditions and diseases, preferably in the form of pharmaceutically acceptable compositions, especially in a method for the therapeutic treatment of the animal or human body, and to such a method of treatment.

The invention relates likewise to pharmaceutical compositions comprising a compound I or a pharmaceutically acceptable salt thereof as active ingredient, and to processes for the manufacture thereof. Those pharmaceutical compositions are compositions for enteral, such as oral and also rectal, administration, for parenteral administration, for local administration and especially for administration by inhalation to warm-blooded animals, especially human beings, the compositions comprising the pharmacological active ingredient alone or together with customary pharmaceutical excipients. The pharmaceutical compositions comprise (in % by weight), for example, from approximately 0.001% to 100%, preferably from approximately 0.1% to approximately 50%, active ingredient.

Pharmaceutical compositions for enteral and parenteral administration are, for example, those in unit dose forms, such as dragées, tablets, capsules or suppositories, and also ampoules. They are manufactured in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture and processing the mixture or granules, if desired or necessary after the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose and/or polyvinylpyrrolidone, and, if desired, disintegrators, such as the above-mentioned starches, and also carboxymethyl starch, cross-linked polyvinylpyrrolidone, agar, or alginic acid or a salt thereof, such as sodium alginate. Excipients are especially flow-conditioners and lubricants, for example silicic acid, talc, stearic acid or salts thereof, such as magnesium or calcium stearate, and/or polyethylene glycol. Dragée cores are provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Other orally administrable pharmaceutical compositions are hard gelatin capsules and also soft, sealed capsules consisting of gelatin and a plasticiser, such as glycerol or sorbitol. The hard gelatin capsules may comprise the active ingredient in the form of granules, for example in admixture with fillers, such as lactose, binders, such as starches, and/or glidants, such as talc or magnesium stearate, and, if desired, stabilisers. In soft capsules the active ingredient is preferably dissolved or suspended in suitable liquids, such as fatty oils, paraffin oil or liquid polyethylene glycols, it likewise being possible to add stabilisers.

Suitable rectally administrable pharmaceutical compositions are, for example, suppositories that consist of a combination of the active ingredient with a suppository base material.

Suitable suppository base materials are, for example, natural or synthetic triglycerides, paraffin hydrocarbons, polyethylene glycols or higher alkanols. It is also possible to use gelatin rectal capsules which comprise a combination of the active ingredient with a base material. Suitable base materials are, for example, liquid triglycerides, polyethylene glycols or paraffin hydrocarbons.

For parenteral administration there are suitable, especially, aqueous solutions of an active ingredient in water-soluble form, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions which comprise viscosity-increasing substances, for example sodium carboxymethylcellulose, sorbitol and/or dextran, and optionally also stabilisers.

Pharmaceutical compositions for local administration are, for example, for the topical treatment of the skin: lotions, creams and ointments, that is to say liquid or semi-solid oil-in-water or water-in-oil emulsions; fatty ointments which are anhydrous; pastes, that is to say creams and ointments having secretion-absorbing powder constituents; gels which are aqueous, have a low water content or contain no water and consist of swellable, gel-forming materials; foams, that is to say liquid oil-in-water emulsions in aerosol form which are administered from pressurised containers; and tinctures having an aqueous-ethanolic base; each of which compositions may comprise further customary pharmaceutical excipients, such as preservatives. The pharmaceutical compositions for local administration are manufactured in a manner known per se by mixing the active ingredient with the pharmaceutical excipients, for example by dissolving or suspending the active ingredient in the base material or, if necessary, in a portion thereof. For the preparation of emulsions in which the active ingredient is dissolved in one of the liquid phases, the active ingredient is usually dissolved in that phase prior to emulsification; for the preparation of suspensions in which the active ingredient is suspended in the emulsion, the active ingredient is mixed with a portion of the base material after emulsification and then added to the remainder of the formulation.

The dosage of the active ingredient can depend on various factors, such as the activity and duration of action of the active ingredient, the severity of the disease to be treated and its symptoms, the mode of administration, the species, sex, age and weight of the warm-blooded animal and/or its individual condition. In a normal case the daily dose for administration, for example oral administration, to a warm-blooded animal weighing about 75 kg is estimated to be from approximately 1 mg to approximately 1000 mg, especially from approximately 5 mg to approximately 200 mg. That dose may be administered, for example, in a single dose or in several part doses of, for example, from 10 to 100 mg.

The following Examples illustrate the invention described above. Temperatures are given in degrees Celsius; DMSO=dimethyl sulfoxide; THF=tetrahydrofuran; EtOH=ethanol; carbamoyl=—$CONH_2$; hexane indicates an isomeric mixture of various hexanes (for example supplied by Fluka); TLC=thin-layer chromatography; RT=room temperature.

EXAMPLE 1

(4R)-[N'-Methyl-N'-(3,5-bistrifluoromethyl-benzoyl)-amino]-5-(1-methyl-indol-3-yl)-pent-2-enoic acid N-[(R)-epsilon-caprolactam-3-yl]-amide 0.525 ml of 3,5-bistrifluoromethyl-benzoyl chloride is added dropwise at 0° to a solution of 0.976 g of (4R)-(N'- methyl-amino)-5-(1-methyl-indol-3-yl)-pent-2-enoic acid N-[(R)-epsilon-caprolactam-3-yl]-amide and 1.1 ml of triethylamine in 20 ml of methylene chloride. The reaction mixture is stirred at 20° for 30 min. and concentrated by evaporation. The residue is taken up in ethyl acetate, and extracted once with water and twice with brine. The combined organic phases are dried over magnesium sulfate and concentrated by evaporation. The residue is subjected to flash chromatography (85 g of silica gel, ethyl acetate/acetone=3/1). The title compound is thus obtained in the form of a colourless solid foam. $R_f$ (ethyl acetate/acetone=1/1)=0.4. HPLC: Chiralcel OD, heptane/isopropyl alcohol =80/20+0.1% trifluoroacetic acid, 1 ml/min., $R_t$=24.39 min. $[\alpha]_D^{20}$=+54.2°+3.8+(c=0.26, EtOH).

The starting materials can be prepared as follows:

a) (4R)-(N'-Methyl-amino)-5-(1-methyl-indol-3-yl)-pent-2-enoic acid N-[(R)-epsilon-caprolactam-3-yl]-amide 27 ml of 4N hydrochloric acid in dioxane are added at 0° to 1.24 g of (4R)-(N'-methyl-N'-tert-butyloxycarbonyl-amino)-5-(1-methyl-indol-3-yl)-pent-2-enoic acid N-[(R)-epsilon-caprolactam-3-yl]-amide. The resulting suspension is stirred at room temperature for 15 min. and concentrated by evaporation. The residue is dissolved in a small amount of ice/water; 2N sodium carbonate solution is added and extraction is carried out three times with ethyl acetate. The combined organic phases are washed twice with brine, dried over magnesium sulfate and concentrated by evaporation. The residue is dissolved twice in methylene chloride and again concentrated by evaporation. The title compound is thus obtained in the form of a yellow foam. $R_f$ (ethyl acetate)=0.05.

b) (4R)-(N'-Methyl-N'-tert-butyloxycarbonyl-amino)-5-(1-methyl-indol-3-yl)-pent-2-enoic acid N-[(R)-epsilon-caprolactam-3-yl]-amide A mixture of 1.07 g of (4R)-(N-methyl-N-tert-butyloxycarbonyl-amino)-5-(1-methyl-indol-3-yl)-pent-2-enoic acid, 0.42 g of D-3-amino-epsilon-caprolactam, 0.63 g of N-ethyl-N'-(3-dimethylamino-propyl)-carbodiimide hydrochloride, 0.48 g of 4-dimethylaminopyridine and 15 ml of methylene chloride is stirred at room temperature for 4 hours and then concentrated by evaporation. The residue is taken up in ethyl acetate, and extracted twice with water, once with 1N hydrochloric acid and twice with brine. The combined organic phases are dried over magnesium sulfate and concentrated by evaporation. In that manner the title compound is obtained in the form of a colourless foam. $R_f$ (methylene chloride/methanol=9/1)=0.45.

c) (4R)-(N-Methyl-N-tert-butyloxycarbonyl-amino)-5-(1-methyl-indol-3-yl)-pent-2-enoic acid A solution of 4.26 g of lithium hydroxide in 27 ml of water is added at 0° to a solution of 5.56 g of (4R)-(N-methyl-N-tert-butyloxycarbonyl-amino)-5-(1-methyl-indol-3-yl)-pent-2-enoic acid ethyl ester in 64 ml of tetrahydrofuran and 64 ml of methanol, and the mixture is stirred at room temperature for 45 min., neutralised with approximately 25 ml of 4N hydrochloric acid and concentrated by evaporation. The residue is taken up in water, acidified to pH=2 with 4N hydrochloric acid and extracted with ethyl acetate. The combined organic phases are washed with water and sat. NaCl solution, dried (magnesium sulfate) and concentrated by evaporation. The residue is dissolved in methylene chloride three times and again concentrated by evaporation. The title compound is thus obtained in the form of a solid foam.

$R_f$ (ethyl acetate/hexane=1/1)=0.07.

d) (4R)-(N -Methyl-N-tert-butyloxycarbonyl-amino)-5-(1-methyl-indol-3-yl)-pent-2-enoic acid ethyl ester 0.848 g of dried LiCl, 1.77 g of 1,8-diazabicyclo[5.4.0] undec-7-ene (DBU), and a solution of 5.75 g of (R)-N-methyl-N-tert-butyloxycarbonyl-amino-3-(1-methyl-indol-3-yl)-propanal in 100 ml of acetonitrile are added at 0° to a solution of 4.86 g of phosphonoacetic acid triethyl ester in 50 ml of absolute acetonitrile. When the addition is complete, the mixture is stirred at room temperature for 45 min. The resulting suspension is then poured into water and extracted twice using 500 ml of diethyl ether each time. The combined organic phases are washed three times with water and twice with sat. NaCl solution, dried (magnesium sulfate) and concentrated by evaporation. The residue is purified by chromatography (330 g of silica gel, hexane/ethyl acetate= 2/1). In that manner the title compound is obtained in the form of a colourless resin. $R_f$ (hexane/ethyl acetate=2/1)= 0.25.

e) (R)-N-Methyl-N-tert-butyloxycarbonyl-amino-3-(1-methyl-indol-3-yl)-propanal A solution of 6.28 g of (R)-N-methyl-N-tert-butyloxycarbonyl-amino-3-(1-methyl-indol-3-yl)-propane-carboxylic acid methyl ester in 117 ml of toluene is cooled to −78° under argon, and 41.6 ml of a 20% diisobutylaluminium hydride solution in toluene are added dropwise thereto (40 min.). When the dropwise addition is complete, the mixture is stirred at −78° for a further 90 min. There are then added 5.9 ml of methanol and 200 ml of diethyl ether at −74°, and 10 g of citric acid dissolved in 190 ml of water in such a manner that the temperature does not exceed −10°. The mixture is stirred vigorously at 0° for 2 hours. The resulting suspension is filtered with suction. In the filtrate the phases are then separated and the aqueous phase is extracted once more with diethyl ether. The combined organic phases are washed with water and sat. NaCl solution, dried (sodium sulfate) and concentrated by evaporation. The title compound is thus obtained in the form of a viscous oil. $R_f$ (hexane/ethyl acetate=2/1)=0.37.

f) (R)-N-Methyl-N-tert-butyloxycarbonyl-amino-3-(1-methyl-indol-3-yl)-propanecarboxylic acid methyl ester 55 g of silver(I) oxide are added at 5°, with stirring, to a solution of 14.3 g of tert-butyloxycarbonyl-D-tryptophan methyl ester in 90 ml of N,N-dimethylformamide. 44 ml of methyl iodide, and 2 ml of acetic acid (abs.) at 5° are then added. The reaction mixture is stirred at room temperature for 72 hours, then diluted with 1 litre of diethyl ether, filtered and concentrated by evaporation. The residue is taken up in diethyl ether, washed with water and brine, dried over magnesium sulfate and concentrated by evaporation. Chromatography of the residue on 1 kg of silica gel (hexane/ethyl acetate=2/1) yields the title compound in the form of a light-yellow resin. $R_f$ (hexane/ethyl acetate=2/1)=0.27.

g) tert-Butyloxycarbonyl-D-tryptophan methyl ester 10 g of tert-butanol, 10.1 g of BOC-anhydride and 12.27 g of diisopropylethylamine dissolved in 30 ml of tetrahydrofuran are added at 0° to a suspension of 12.12 g of D-tryptophan methyl ester hydrochloride in 80 ml of abs. tetrahydrofuran. After being stirred for two hours at room temperature, the reaction mixture is poured into ice/470 ml of 0.3N HCl and extracted three times with ethyl acetate. The combined organic phases are washed once with water and twice with sat. NaCl solution, dried (MgSO$_4$) and concentrated by evaporation. The residue is made into a slurry in diethyl ether/petroleum ether and filtered with suction. The title compound is thus obtained in the form of colourless crystals having a melting point of 148–1490. R$_f$ (methylene chloride)=0.24.

In the same manner as that described in Example 1 but using the appropriate amines instead of D-3-amino-epsilon-caprolactam, the following compounds can be obtained:

EXAMPLE 2

(4R)-[N'-Methyl-N'-(3,5-bistrifluoromethyl-benzoyl)-amino]-5-(1-methyl-indol-3-yl)-pent-2-enoic acid N-[(S)-epsilon-caprolactam-3-yl]-amide Using L-3-amino-epsilon-caprolactam. Solid foam, R$_f$ (ethyl acetate/acetone=1/1)=0.31, HPLC: Chiralpack OD, heptane/isopropyl alcohol=80/20+0.1% trifluoroacetic acid, 1 ml/min., R$_t$=29.96 min. $[\alpha]_D^{20}$=+67°±2.3° (c=0.44, EtOH).

EXAMPLE 3

(4R)-[N'-Methyl-N'-(3,5-bistrifluoromethyl-benzoyl)-amino]-5-(1-methyl-indol-3-yl)-pent-2-enoic acid N-cyclohexyl-amide Using cyclohexylamine. R$_f$ (ethyl acetate)=0.41.

EXAMPLE 4

(4R)-[N'-Methyl-N'-(3,5-bistrifluoromethyl-benzoyl)-amino]-5-(1-methyl-indol-3-yl)-2-methyl-pent-2-enoic acid N-cyclohexyl-amide The title compound can be prepared in exactly the same manner as that described in Example 1 but using triethyl-2-phosphono-propionate instead of triethylphosphonoacetic acid ester in sub-step 1d). The title compound is obtained in the form of an amorphous colourless solid. R$_f$ (ethyl acetate)=0.46.

Analogously thereto it is also possible to prepare the following products:

EXAMPLE 5

(4R)-[N'-Methyl-N'-(3,5-bistrifluoromethyl-benzoyl)-amino]-5-(1-methyl-indol-3-yl)-2-methyl-pent-2-enoic acid N-[(R)-epsilon-caprolactam-3-yl]-amide Colourless foam, R$_f$ (ethyl acetate/acetone=1/1)=0.46; $[\alpha]_D^{20}$=−24.40+2.8°(c=0.352, EtOH).

EXAMPLE 6

(4R)-[N'-Methyl-N'-(3,5-bistrifluoromethyl-benzoyl)-amino]-5-(1-methyl-indol-3-yl)-2-methyl-pent-2-enoic acid N-[(S)-epsilon-caprolactam-3-yl]-amide Colourless foam, R$_f$ (ethyl acetate/acetone=1/1)=0.46. Using L-3-amino-epsilon-caprolactam.

In the same manner as that described in Example 5 but using benzoyl chloride instead of 3,5-bistrifluoromethyl-benzoyl chloride, the following product can be prepared:

EXAMPLE 5/1

(4R)-(N'-Methyl-N'-benzoyl-amino)-5-(1-methyl-indol-3-yl)-2-methyl-pent-2-enoic acid N-[(R)-epsilon-caprolactam-3-yl]-amide Colourless foam, R$_f$ (ethyl acetate/-acetone=1/1)=0.23; $[\alpha]_D^{20}$=−10.7°+3.5°(c=0.283, EtOH).

EXAMPLE 7

(4R)-[N'-Methyl-N'-(3,5-bistrifluoromethyl-benzoyl)-amino]-5-(naphth-2-yl)-pent-2-enoic acid N-[(R)-epsilon-caprolactam-3-yl]-amide 78.3 mg of (D)-3-amino-epsilon-caprolactam, 116.9 mg of N-ethyl-N'-(3-dimethylamino-propyl)-carbodiimide hydrochloride and 88 mg of 4-dimethylaminopyridine are added to a solution of 0.275 g of (4R)-[N-methyl-N-(3,5-bistrifluoromethyl-benzoyl)-amino]-5-(naphth-2-yl)-pent-2-enoic acid in 6 ml of methylene chloride. The reaction mixture is stirred at 20° for 3.5 hours and concentrated by evaporation. The residue is subjected to flash chromatography (40 g of silica gel, ethyl acetate). The title compound is thus obtained in the form of a light-yellow solid. R$_f$ (methylene chloride/methanol=15/1)=0.28.

The starting materials can be prepared as follows:

a) (4R)-[N-Methyl-N-(3,5-bistrifluoromethyl-benzoyl)-amino]-5-(naphth-2-yl)-pent-2-enoic acid A solution of 0.18 g of lithium hydroxide in 1.18 ml of water is added at 0° to a solution of 0.325 g of (4R)-[N-methyl-N-(3,5-bistrifluoromethyl-benzoyl)-amino]-5-(naphth-2-yl)-pent-2-enoic acid ethyl ester in 3 ml of tetrahydrofuran and 3 ml of methanol, and the mixture is stirred at room temperature for 45 min., neutralised with a small amount of 4N hydrochloric acid and concentrated by evaporation. The residue is taken up in water, acidified to pH=2 with 4N hydrochloric acid and extracted with ethyl acetate. The combined organic phases are washed with water and sat. NaCl solution, dried (magnesium sulfate) and concentrated by evaporation. The residue is dissolved three times in methylene chloride and again concentrated by evaporation. The title compound is thus obtained in the form of a colourless solid foam. R$_f$ (ethyl acetate/hexane=1/1)=0.15.

b) (4R)-[N-Methyl-N-(3,5-bistrifluoromethyl-benzoyl)-amino]-5-(naphth-2-yl)-pent-2-enoic acid ethyl ester 0.229 ml of 3,5-bistrifluoromethyl-benzoyl chloride are added dropwise at 0° to a solution of 0.327 g of (4R)-N-methyl-amino-5-(naphth-2-yl)-pent-2-enoic acid ethyl ester and 0.48 ml of triethylamine in 5 ml of methylene chloride. The reaction mixture is stirred at 20° for 60 min. and concentrated by evaporation. The residue is taken up in ethyl acetate, and extracted once with water and twice with brine. The combined organic phases are dried over magnesium sulfate and concentrated by evaporation. The residue is subjected to flash chromatography (40 g of silica gel, hexane/ethyl acetate=2/1). The title compound is thus obtained in the form of a solid orange foam. R$_f$(hexane/ethyl acetate=2/1)=0.59.

c) (4R)-N-Methyl-amino-5-(naphth-2-yl)-pent-2-enoic acid ethyl ester 8 ml of 4N hydrochloric acid in dioxane are added at 0° to 0.30 g of (4R)-(N-methyl-N-tert-butyloxycarbonyl-amino)-5-(naphth-2-yl)-pent-2-enoic acid ethyl ester. The resulting suspension is stirred at room temperature for 20 min. and concentrated by evaporation. The residue is dissolved in a small amount of ice/water; 2N sodium carbonate solution is added and extraction is carried out three times with ethyl acetate. The combined organic phases are washed twice with brine, dried over magnesium sulfate and concentrated by evaporation. The residue is dissolved twice in methylene chloride and again concentrated by evaporation. The title compound is thus obtained in the form of a yellow foam. $R_f$ (ethyl acetate)=0.65.

d) (4R)-(N-Methyl-N-tert-butyloxycarbonyl-amino)-5-(naphth-2-yl)-pent-2-enoic acid ethyl ester 1.34 g of dried LiCl, 4.37 g of 1,8-diazabicyclo[5.4.0]undec-7-ene (DBU), and a solution of 9.0 g of (R)-(N-methyl-N-tert-butyloxycarbonyl-amino)-3-(naphth-2-yl)-propanal in 150 ml of acetonitrile are added at 0° to a solution of 7.08 g of phosphonoacetic acid triethyl ester in 80 ml of absolute acetonitrile. When the addition is complete, the mixture is stirred at room temperature for a further 45 min. The resulting suspension is then poured into water and extracted twice using 600 ml of diethyl ether each time. The combined organic phases are washed three times with water and twice with sat. NaCl solution, dried (magnesium sulfate) and concentrated by evaporation. The residue is purified by chromatography (800 g of silica gel, hexane/ethyl acetate=8/1). In that manner the title compound is obtained in the form of a colourless resin. $R_f$ (hexane/ethyl acetate=8/1)=0.09. HPLC: Chiralcel OJ, hexane/isopropyl alcohol=90/10+0.1% trifluoroacetic acid, 1 ml/min., $R_t$=15.86 min.

e) (R)-(N-Methyl-N-tert-butyloxycarbonyl-amino)-3-(naphth-2-yl)-propanal

A solution of 21.8 g of (R)-N-methyl-N-tert-butyloxycarbonyl-amino-3-(naphth-2-yl)-propanecarboxylic acid methyl ester in 497 ml of toluene is cooled to −78° under argon, and 146 ml of a 20% diisobutylaluminium hydride solution in toluene are added dropwise thereto (60 min.). When the dropwise addition is complete, the mixture is stirred at −78° for a further 60 min. There are then added 17.8 ml of methanol at −74°, and 35 g of citric acid dissolved in 665 ml of water in such a manner that the temperature does not exceed −10°. The mixture is stirred vigorously at 0° for 2 hours and diluted with diethyl ether. The resulting suspension is filtered with suction. In the filtrate the phases are then separated and the aqueous phase is extracted once more with diethyl ether. The combined organic phases are washed with water and sat. NaCl solution, dried (sodium sulfate) and concentrated by evaporation. The title compound is thus obtained in the form of beige crystals having a melting point of 98–100°. $R_f$ (hexane/ethyl acetate=3/2)=0.51.

f) (R)-N-Methyl-N-tert-butyloxycarbonyl-amino-3-(naphth-2-yl)-propanecarboxylic acid methyl ester 76.4 g of silver(1) oxide are added at 5°, with stirring, to a solution of 20.1 g of (R)-N-tert-butyloxy-carbonyl-amino-3-(naphth-2-yl)-propanecarboxylic acid (e.g. Bachem) in 191 ml of N,N-dimethylformamide. 12.5 ml of methyl iodide are then added at 5°. The reaction mixture is stirred at room temperature for 24 hours, then diluted with 1 litre of diethyl ether, filtered and concentrated by evaporation. The residue is taken up in diethyl ether, washed with water and brine, dried over magnesium sulfate and concentrated by evaporation. The title compound is thus obtained in the form of a light-yellow oil. $R_f$ (hexane/ethyl acetate=4/1)=0.47. HPLC: Chiralcel OJ, hexane/isopropyl alcohol=90/10±0.1% trifluoroacetic acid, 1 ml/min., $R_t$=11.32 min.

In the same manner as that described in Example 7 but using benzoyl chloride instead of 3,5-bistrifluoromethyl-benzoyl chloride in Step 7b), the following product is obtained:

EXAMPLE 7/1

(4R)-(N'-Methyl-N'-benzoyl)-amino-5-(naphth-2-yl)-pent-2-enoic acid N-[(R)-epsilon-caprolactam-3-yl]-amide $R_f$ (ethyl acetate/acetone=9/1)=0.13.

EXAMPLE 8

(4R)-[N'-Methyl-N'-(3,5-bistrifluoromethyl-benzoyl)-amino]-5-(naphth-2-yl)-2-methyl-pent-2-enoic acid N-[(R)-epsilon-caprolactam-3-yl]-amide 0.153 ml of 3,5-bistrifluoromethyl-benzoyl chloride are added dropwise at 0° to a solution of 0.27 g of (4R)-(N'-methyl-amino)-5-(naphth-2-yl)-2-methyl-pent-2-enoic acid N-[(R)-epsilon-caprolactam-3-yl]-amide and 0.3 ml of triethylamine in 6 ml of methylene chloride. The reaction mixture is stirred at 20° for 90 min. and concentrated by evaporation. The residue is taken up in ethyl acetate, and extracted once with water and twice with brine. The combined organic phases are dried over magnesium sulfate and concentrated by evaporation. The residue is subjected to flash chromatography (150 g of silica gel, ethyl acetate/hexane=4/1). The title compound is thus obtained in the form of a colourless solid foam. $R_f$ (ethyl acetate)=0.43. HPLC: AD column, hexane/isopropyl alcohol=90/10+0.1% trifluoroacetic acid, 1 ml/min., $R_t$=17.87 min.

The starting materials can be prepared as follows:

a) (4R)-(N'-Methyl-amino)-5-(naphth-2-yl)-2-methyl-pent-2-enoic acid N-[(R)-epsilon-caprolactam-3-yl]-amide 7.0 ml of 4N hydrochloric acid in dioxane are added at 0° to 0.342 g of (4R)-(N'-methyl-N'-tert-butyloxycarbonyl-amino)-5-(naphth-2-yl)-2-methyl-pent-2-enoic acid N-[(R)-epsilon-caprolactam-3-yl]-amide. The resulting suspension is stirred at room temperature for 20 min. and concentrated by evaporation. The residue is dissolved in a small amount of ice/water; 2N sodium carbonate solution is added and extraction is carried out three times with ethyl acetate. The combined organic phases are washed twice with brine, dried over magnesium sulfate and concentrated by evaporation. The residue is dissolved twice in methylene chloride and again concentrated by evaporation. The title compound is thus obtained in the form of a yellow foam. $R_f$ (methylene chloride/methanol=95/5)=0.33.

b) (4R)-(N'-Methyl-N'-tert-butylcarbonyl-amino)-5-(naphth-2-yl)-2-methyl-pent-2-enoic acid N-[(R)-epsilon-caprolactam-3-yl]-amide A mixture of 500 mg of (4R)-(N-methyl-N-tert-butyloxycarbonyl-amino)-5-(naphth-2-yl)-2-methyl-pent-2-enoic acid, 0.183 g of D-3-amino-epsilon-caprolactam, 0.265 g of N-ethyl-N'-(3-dimethylamino-propyl)-carbodiimide hydrochloride, 0.200 g of 4-dimethylaminopyridine and 16 ml of methylene chloride is stirred at room temperature for 1 hour and then concentrated by evaporation. The residue is taken up in ethyl acetate, and extracted twice with water, once with 1N hydrochloric acid and twice with brine. The combined organic phases are dried over magnesium sulfate and concentrated by evaporation. The residue is subjected to flash chromatography (80 g of silica gel, ethyl acetate/hexane=7/3–9/1). In that manner the title compound is obtained in the form of a colourless foam. $R_f$ (ethyl acetate)=0.39.

c) (4R)-(N-Methyl-N-tert-butyloxycarbonyl-amino)-5-(naphth-2-yl)-2-methyl-pent-2-enoic acid A solution of 2.6 g of lithium hydroxide in 17 ml of water is added at 0° to a solution of 3.5 g of (4R)-(N-methyl-N- tert-butyloxy-carbonyl-amino)-5-(naphth-2-yl)-2-methyl-pent-2-enoic acid ethyl ester in 40 ml of tetrahydrofuran and 40 ml of methanol, and the mixture is stirred at room temperature for 45 min., neutralised with approximately 15 ml of 4N hydrochloric acid and concentrated by evaporation. The residue is taken up in water, acidified to pH=2 with 4N hydrochloric acid and extracted with ethyl acetate. The combined organic phases are washed with water and sat. NaCl solution, dried (magnesium sulfate) and concentrated by evaporation. The residue is dissolved three times in methylene chloride and again concentrated by evaporation. The title compound is thus obtained in the form of a solid foam. $R_f$ (ethyl acetate/hexane=1/1)=0.26.

d) (4R)-(N-Methyl-N-tert-butyloxycarbonyl-amino)-5-(naphth-2-yl)-2-methyl-pent-2-enoic acid ethyl ester 1.36 g of dried LiCl, 4.37 g of 1,8-diazabicyclo[5.4.0]undec-7-ene (DBU), and a solution of 9 g of (R)-N-methyl-N-tert-butyloxycarbonyl-amino-3-(naphth-2-yl)-propanal in 150 ml of acetonitrile are added at 0° to a solution of 7.52 g of 2-phosphono-propionic acid triethyl ester in 80 ml of absolute acetonitrile. When the addition is complete, the mixture is stirred at 100 for 40 min. The resulting suspension is then poured into water and extracted twice using 600 ml of diethyl ether each time. The combined organic phases are washed three times with water and twice with sat. NaCl solution, dried (magnesium sulfate) and concentrated by evaporation. The residue is purified by chromatography (600 g of silica gel, hexane/ethyl acetate=95/5–93/7). In that manner the title compound is obtained in the form of a colourless resin. $R_f$ (hexane/ethyl acetate=7/3)=0.53.

In the same manner as that described in Example 8 but using 3,4,5-trimethoxy-benzoyl chloride instead of 3,5-bistrifluoromethyl-benzoyl chloride, the following product can be prepared:

EXAMPLE 8/1

(4R)-[N'-Methyl-N'-(3,4,5-trimethoxy-benzoyl)-amino]-5-(naphth-2-yl)-2-methyl-pent-2-enoic acid N-[(R)-epsilon-caprolactam-3-yl]-amide $R_f$ (methylene chloride/methanol=95/5)=0.42.

In the same manner as that described in Example 8 but using the appropriate amines instead of D-3-amino-epsilon-caprolactam, the following products can be obtained:

EXAMPLE 9

(4 R)-[N'-Methyl-N'-(3,5-bistrifluoromethyl-benzoyl)-amino]-5-(naphth-2-yl)-2-methyl-pent-2-enoic acid N-[(S)-epsilon-caprolactam-3-yl]-amide Using L-3-amino-epsilon-caprolactam. $R_f$ (ethyl acetate)=0.44.

EXAMPLE 10

(4R)-[N'-Methyl-N'-(3,5-bistrifluoromethyl-benzoyl)-amino]-5-(naphth-2-yl)-2-methyl-pent-2-enoic acid N-cyclohexyl-amide Using cyclohexylamine. $R_f$ (hexane/ethyl acetate=1/1)= 0.43. HPLC: Chiralcel AD, hexane/isopropyl alcohol=90/10+0.1% trifluoroacetic acid, 1 ml/min., $R_t$=6.25 min.

EXAMPLE 11

(4R)-[N'-Methyl-N'-(3,5-bistrifluoromethyl-benzoyl)-amino]-5-(1-methyl-indol-3-yl)-pent-2-enoic acid N-[(S)-epsilon-caprolactam-3-yl]-amide (another preparation method for the compound of Example 2)

The title compound can also be prepared starting from racemic D,L-tryptophan methyl ester hydrochloride (instead of D-tryptophan methyl ester hydrochloride). D,L-Tryptophan methyl ester hydrochloride is reacted in a manner analogous to that described in Example 1. L-3-Amino-epsilon-caprolactam is used in Step 1b). The resulting mixture of diastereoisomers is then separated in a final step by chromatography on silica gel (ethyl acetate). In that manner (4R)-[N'-methyl-N'-(3,5-bistrifluoromethyl-benzoyl)-amino]-5-(1-methyl-indol-3-yl)-pent-2-enoic acid N-[(S)-epsilon-caprolactam-3-yl]-amide ($R_f$=0.31, ethyl acetate/acetone =1/1) and (S)-4-[N'-methyl-N'-(3,5-bistrifluoromethyl-benzoyl)-amino]-5-(1-methyl-indol-3-yl)-pent-2-enoic acid N-[(S)-epsilon-caprolactam-3-yl]-amide {$R_f$=0.35, ethyl acetate/acetone=1/1; $[\alpha]_D^{20}$= 44.3°4.5°(c=0.221, EtOH)} are obtained in pure form.

EXAMPLE 12

(4R)-[N'-Methyl-N'-(3,5-bistrifluoromethyl-benzoyl)-amino]-4-(4-chlorobenzyl)-but-2-enoic acid N-[(R)-epsilon-caprolactam-3-yl]-amide A solution of 0.71 g of 3,5-bistrifluoromethylbenzoyl chloride (in 5 ml of methylene chloride) is added dropwise at 0° to a solution of 0.9 g of (4R)-(N'-methyl-amino)-4-(4-chlorobenzyl)-but-2-enoic acid N-[(R)-epsilon-caprolactam-3-yl]-amide and 0.75 ml of triethylamine in 35 ml of methylene chloride. The reaction mixture is stirred at room temperature for 2 hours. Then 3 ml of methanol are added and the reaction mixture is diluted with 50 ml of methylene chloride. The solution is washed with 0.1N HCl, water (twice) and sat. NaCl solution, dried (MgSO$_4$) and concentrated by evaporation. The residue is subjected to flash chromatography (85 g of silica gel, ethyl acetate/methanol=98/2). The title compound is obtained in the form of a white amorphous solid. $R_f$=0.12 (ethyl acetate), $[\alpha]_D^{20}$=+42°±1°(c=1, EtOH). $R_t$=20.38 min. (Chiracel-OJ, 0.46×25 cm, detection 210 nm, hexane:ethanol =90:10+ 0.1% TFA, flow rate 1.0 ml/min., 30 bar).

The starting materials can be prepared as follows:

a): (4R)-(N'-Methyl-amino)-4-(4-chlorobenzyl)-but-2-enoic acid N-[(R)-epsilon-caprolactam-3-yl]-amide A solution of 1.2 g of (4R)-(N'-methyl-N'-tert-butyloxycarbonyl-amino)-4-(4-chloro-benzyl)-but-2-enoic acid N-[(R)-epsilon-caprolactam-3-yl]-amide and 8 ml of trifluoroacetic acid in 30 ml of methylene chloride is stirred under argon at room temperature for 2 hours. The reaction mixture is then concentrated by evaporation and dissolved in 200 ml of ethyl acetate. The ethyl acetate solution is washed with 0.05N sodium hydroxide solution and sat. NaCl solution, dried (sodium sulfate), concentrated by evaporation and reacted further without further purification.

b): (4R)-(N'-Methyl-N'-tert-butyloxycarbonyl-amino)-4-(4-chlorobenzyl)-but-2-enoic acid N-[(R)-epsilon-caprolactam-3-yl]-amide A mixture of 1.53 g of (4R)-(N'-methyl-N'-tert-butyl-oxycarbonyl-amino)-4-(4-chlorobenzyl)-but-2-enoic acid, 0.58 g of D-3-amino-epsilon-caprolactam, 0.94 g of N-ethyl-N'-(3-dimethylaminopropyl)-carbodiimide hydrochloride, 0.60 g of 4-dimethylaminopyridine, 0.725 g of hydroxybenzotriazole and 80 ml of methylene chloride is stirred at room temperature for 16 hours and then concentrated by evaporation. The residue is chromatographed (silica gel, hexane/ethyl acetate=1/1). In that manner the title compound is obtained, m.p.: 154–156° C.

c): (4R)-(N'-Methyl-N'-tert-butyloxycarbonyl-amino)-4-(4-chlorobenzyl)-but-2-enoic acid A solution of 1.64 g of (4R)-(N'-methyl-N'-tert-butyloxycarbonyl-amino)-4-(4-chlorobenzyl)-but-2-enoic acid ethyl ester and 1.72 g of lithium hydroxide in tetrahydrofuran/methanol/-water=3/3/1 is stirred at room temperature for 1 hour and then poured into 150 ml of water. The mixture is acidified to pH=2 by the addition of 1N hydrochloric acid and the aqueous phases are extracted twice with diethyl ether. The combined organic phases are washed with water and sat. NaCl solution, dried (magnesium sulfate) and concentrated by evaporation to form a colourless oil. 1H-NMR, 400 MHz, CDCl$_3$, d (ppm): 7.30 (d, 2H), 7.20 (d, 2H), 6.80 (dd,1 H), 5.81 (d, 1H), 4.85 (m,1 H), 2.75 (d, 2H), 2.63 (s, 3H), 1.35 (s, 9H).

d): (4R)-(N'-Methyl-N'-tert-butyloxycarbonyl-amino)-4-(4-chlorobenzyl)-but-2-enoic acid ethyl ester 0.453 g of dried LiCl and 1.46 g of DBU are added at RT to a solution of 2.37 g of phosphonoacetic acid triethyl ester in 40 ml of absolute acetonitrile. Then a solution of 2.86 g of (R)-N'-methyl-N'-tert-butyloxycarbonyl-(4-chlorophenyl)-alaninal (in 10 ml of acetonitrile) is added dropwise thereto. When the dropwise addition is complete, the mixture is stirred at RT for 2 hours. The reaction mixture is then poured into water and extracted twice using 100 ml of diethyl ether each time. The combined organic phases are washed three times with water and once with sat. NaCl solution, dried (magnesium sulfate) and concentrated by evaporation. The residue is purified by chromatography (silica gel, hexane/ethyl acetate=3/1). In that manner the title compound is obtained in the form of a colourless oil. 1H-NMR, 200 MHz, CDCl$_3$, d (ppm): 7.35–7.05 (m, 4H), 6.90 (dd, 1H), 5.85 (d, 1H), 5.15 (m, 0.5H), 4.90 (m, 0.5H), 4.17 (q, 2H), 2.90 (m, 2H), 2.68 (s, 3H), 1.30 (m, 12H).

e): (R)-N'-Methyl-N'-tert-butyloxycarbonyl-(4-chlorophenyl)-alaninal

A solution of 2.95 g of (R)-N'-methyl-N'-tert-butyloxycarbonyl-(4-chlorophenyl)-alanine methyl ester in 75 ml of toluene is cooled to −78° under argon. At that temperature 17 ml of a 1M DIBAH solution (in toluene) are slowly added dropwise thereto. When the dropwise addition is complete, the mixture is stirred at that temperature for 2 hours. 2 ml of methanol and 50 ml (18 g) of an aqueous sodium/potassium tartrate solution are then added to the reaction mixture. The mixture is stirred vigorously at 0° for 2 hours. The phases are then separated and the aqueous phase is extracted once more with diethyl ether. The combined organic phases are washed with water and sat. NaCl solution, dried (sodium sulfate) and concentrated by evaporation. The residue is reacted further without purification (colourless oil). $^1$H-NMR, 200 MHz, CDCl$_3$, d (ppm): 7.30–7.05 (m, 4H), 4.16 (m, 0.5H), 3.93 (m, 0.5H), 3.25 (dd, 2H), 2.90 (m, 1H), 2.70 and 2.62 (2s, 3H), 1.40 (2s, 9H).

f): (R)-N'-Methyl-N'-tert-butyloxycarbonyl-(4-chlorophenyl)-alanine methyl ester 9.5 g of silver(1) oxide are added, with stirring, to a solution of 3.1 g of (R)-tert-butyloxycarbonyl-(4-chlorophenyl)-alanine methyl ester in 45 ml of N,N-dimethylformamide. 23 g of methyl iodide and 1 ml of acetic acid (abs.) are then added. The reaction mixture is stirred at RT for 72 hours, then diluted with 150 ml of diethyl ether, filtered and concentrated by evaporation. The residue is purified by chromatography (silica gel, hexane/ethyl acetate=5/1). In that manner the title compound is obtained in the form of a colourless oil. $^1$H-NMR: 7.25 (d, 2H), 7.11 (d, 2H), 4.90 (bs, 0.5H), 4.47 (bs, 0.5H), 3.72 (s, 3H), 3.25 (m, 1H), 3.00 (dd, 1H), 2.70 (s, 3H) 1.35 (s, 9H).

g): (R)-tert-Butyloxycarbonyl-(4-chlorophenyl)-alanine methyl ester 4 ml of tert-butanol, 2.12 g of BOC-anhydride and 2.57 g of diisopropylethylamine are added to a suspension of 2.5 g of D-4-chlorophenylalanine methyl ester (e.g. Bachem) in 40 ml of abs. THF. After being stirred for 4 hours at room temperature, the reaction mixture is poured into ice/0.1N HCl and extracted twice with diethyl ether. The combined organic phases are washed with water (three times) and sat. NaCl solution, dried (MgSO$_4$) and concentrated by evaporation to form an oil which crystallises completely on being left to stand. R$_f$=0.19 (hexane:ethyl acetate=5:1).

Preparation of D-3-amino-epsilon-caprolactam

A solution of 12.8 g of D,L-3-amino-epsilon-caprolactam in 200 ml of abs. ethanol is mixed with a solution of 12.9 g of D-pyroglutamic acid (in 200 ml of abs. ethanol) and left to stand at room temperature for 20 hours. The resulting crystals are filtered off and dissolved at about 65–70° C. in ethanol:water=9:1, cooled to room temperature and again left to stand for 20 hours. The crystals formed there-from are filtered off and dissolved in 50 ml of water. Ion exchange chromatography (DOWEX 50W, acidic form, elution of the free base with 1N NH$_3$ solution) yields the title compound in the form of the free amine. Colourless crystals. $[\alpha]_D^{20}$=+ 41°(c=2.2, water). In the same manner as that described in Example 12 but using the appropriate amines (instead of D-3-amino-epsilon-caprolactam) in Step 12b), the following products are also obtained:

EXAMPLE 13

(4R)-[N'-Methyl-N'-(3,5-bistrifluoromethyl-benzoyl)-amino]-4-(4-chlorobenzyl-but-2-enoic acid N-[(S)-epsilon-caprolactam-3-yl]-amide R$_f$=0.12 (ethyl acetate). Using L-3-amino-epsilon-caprolactam (commercially available, e.g.: Fluka 07257). R$_t$=35.2 min. (Chiracel-OD, 0.46×25 cm, detection 210 nm, hexane:isopropanol=80:20+0.1% TFA, flow rate 1.0 ml/min., 30 bar).

EXAMPLE 14

(4R)-[N'-Methyl-N'-(3,5-bistrifluoromethyl-benzoyl)-amino]-4-(4-chlorobenzyl-but-2-enoic acid N-cyclohexyl-amide m.p. 183–185° C.

Using cyclohexylamine. R$_t$=10.5 min. (Chiracel-AC, 0.46×25 cm, detection 210 nm, hexane:isopropyl alcohol= 97:3+0.1% TFA, flow rate 1.0 ml/min., 20 bar). $[\alpha]_D^{20}$=+ 60.40+4.4°(c=0.227, EtOH).

Analogously to the procedure described under Examples 12 and 14 it is also possible, starting from the appropriately halogenated phenylalanine derivatives, to prepare the following substances:

EXAMPLE 14A (4R)-[N'-Methyl-N'-(3,5-bistrifluoromethyl-benzoyl)-amino]-4-(3,4-dichlorobenzyl)-but-2-enoic acid N-cyclohexyl-amide $R_f$=0.24 (hexane:ethyl acetate=1:1).

EXAMPLE 14B (4R)-[N'-Methyl-N'-(3,5-bistrifluoromethyl-benzoyl)-amino]-4-(3,4-difluorobenzyl)-but-2-enoic acid N-cyclohexyl-amide $R_f$=0.28 (hexane:ethyl acetate=1:1). EXAMPLE 15

(4R)-[N'-Methyl-N'-(3,5-bistrifluoromethyl-benzoyl)-amino]-5-(4-chlorophenyl)-2-methyl-pent-2-enoic acid N-cyclohexylamide The title compound is prepared in exactly the same manner as that described in Example 14 (and Example 12, respectively) but using triethyl 2-phosphono-propionate instead of triethyl phosphonoacetic acid ester in sub-step 12d). The title compound is obtained in the form of an amorphous colourless solid. $R_f$=0.32 (hexane:ethyl acetate= 1:1).

Analogously to Example 15 it is also possible to prepare the following products:

EXAMPLE 16

(4R)-[N'-Methyl-N'-(3,5-bistrifluoromethyl-benzoyl)-amino]-5-(4-chlorophenyl)-2-methyl-pent-2-enoic acid N-[(R)-epsilon-caprolactam-3-yl]-amide $R_f$=0.14 (ethyl acetate). Using D-3-amino-epsilon-caprolactam. $R_t$=6.24 min. (Chiracel-AD, 0.46×25 cm, detection 210 nm, hexane:ethanol=98:2 +0.1% TFA, flow rate 1.0 ml/min., 30 bar). $[\alpha]_D^{20}$=−10.70°±4.4°(c=0.225, EtOH)

EXAMPLE 17

(4R)-[N'-Methyl-N'-(3,5-bistrifluoromethyl-benzoyl)-amino]-4-(4-chlorobenzyl)-2-methyl-but-2-enoic acid [(S)-epsilon-caprolactam-3-yl]-amide $R_f$=0.14 (ethyl acetate). Using L-3-amino-epsilon-caprolactam.

EXAMPLE 18

(4R)-[N'-Ethyl-N'-(3,5-bistrifluoromethyl-benzoyl)-amino]-5-(4-chlorophenyl)-pent-2-enoic acid N-[(S)-epsilon-caprolactam-3-yl]-amide The title compound is prepared starting from (R)-N-ethyl-N-tert-butyloxycarbonyl-(4-chlorophenyl)-alanine methyl ester in exactly the same manner (using L-3-amino-epsilon-caprolactam) as that described in Example 12. $R_f$=0.18 (ethyl acetate).

The starting material (R)-N-ethyl-N-tert-butyloxycarbonyl-(4-chlorophenyl)-alanine methyl ester can be prepared as follows: 118 mg of sodium hydride (pure) are added in portions at 0° under argon to a solution of 1.4 g of N-tert-butyloxycarbonyl-(4-chlorophenyl)-alanine methyl ester in 25 ml of DMF. The mixture is stirred at 0C for 30 min. and at RT for 30 min. Then 1.07 g of ethyl bromide are added and the reaction mixture is stirred at 50° C. for 16 hours. The reaction mixture is then poured into 200 ml of water and the aqueous phase is extracted twice with diethyl ether. The combined organic phases are washed with water and sat. sodium chloride solution, dried (MgSO$_4$) and concentrated by evaporation. The residue is chromatographed (hexane/ethyl acetate=5/1). In that manner the title compound is obtained in the form of a colourless oil.

EXAMPLE 19

(4R)-[N'-Methyl-N'-(3,5-bistrifluoromethyl-benzoyl)-amino]-5-(4-chlorophenyl)-3-methyl-pent-2-enoic acid N-cyclohexyl-amide The title compound can be prepared in exactly the same manner as that described in Example 12 but starting from (R)-[1-(4-chloro-benzyl)- 2-oxo-propyl]-carbamic acid tert-butyl ester instead of (R)-N'-methyl-N'-tert-butyloxy-carbonyl-(4-chlorophenyl)-alaninal. $R_f$=0.41 (hexane:ethyl acetate 1:1).

The starting material, (R)-[1-(4-chloro-benzyl)-2-oxo-propyl]-carbamic acid tert-butyl ester, can be prepared as follows: a solution of 0.77 ml of DMSO (in 2.5 ml of methylene chloride) is added dropwise in the course of 5 min. at −60° C. under argon to a solution of 0.45 ml of oxalyl chloride (in 10 ml of methylene chloride), and the mixture is then stirred for 15 min. Likewise at −60° C., a solution of 1.4 g of (R)-[1-(4-chloro-benzyl)-2-hydroxy-propyl]-carbamic acid tert-butyl ester (in 4 ml of methylene chloride) is then added dropwise thereto. The reaction mixture is stirred for 1 hour; triethylamine is added and the mixture is heated to room temperature, at which temperature 25 ml of water are added. The organic phase is separated off and the aqueous phase is extracted twice m ore with methylene chloride. The combined organic phases are washed with water and saturated sodium chloride solution, dried (MgSO$_4$) and concentrated by evaporation. The residue is subjected to flash chromatography (toluene/methylene chloride/ethyl acetate=4/4/2). In that manner the title compound is obtained in the form of a colourless oil.

(R)-[1-(4-Chloro-benzyl)-2-hydroxy-propyl]-carbamic acid tert-butyl ester 10 ml of a Grignard solution (prepared from 0.64 ml of methyl iodide and 0.244 g of magnesium turning s in 20 ml of diethyl ether) are added dropwise to a solution of 1.19 g of (R)-N'-methyl-N'-tert-butyloxycarbonyl-(4-chlorophenyl)-alaninal in 25 ml of THF and the mixture is then stirred for 30 min. The reaction mixture is then poured into 100 ml of water and extracted twice with diethyl ether. The combined organic phases are washed with water and saturated sodium chloride solution, dried (MgSO$_4$) and concentrated by evaporation. The residue is subjected to flash chromatography (hexane/ethyl acetate=1/1). In that manner the title compound i s obtained in the form of a colourless oil.

Analogously to Example 19, using D-3-amino-epsilon-caprolactam instead of cyclohexyl-amine, i t is also possible to obtain the following compound:

EXAMPLE 20

(4R)-[N'-Methyl-N'-(3,5-bistrifluoromethyl-benzoyl)-amino]-4-(4-chlorobenzyl)-3-methyl-but-2-enoic acid [(R)-epsilon-caprolactam-3-yl]-amide Using D-3-amino-epsilon-caprolactam. $R_f$=0.16 (ethyl acetate).

EXAMPLE 21

(4R)-[N'-Methyl-N'-(3,5-bistrifluoromethyl-benzoyl)-amino]-4-(4-chlorobenzyl-but-2-enoic acid N-[(R)-epsilon-caprolactam-3-yl]-amide (another preparation method for the compound of Example 12).

The title compound can also be prepared starting from racemic 4-chlorophenylalanine methyl ester (instead of D-4-chlorophenylalanine methyl ester). Racemic 4-chlorophenylalanine methyl ester is reacted in a manner analogous to that described in Example 12. In Step b), D-3-amino-epsilon-caprolactam is used, as in Step 12b). The resulting mixture of diastereoisomers is then separated in a final step by chromatography on silica gel (ethyl acetate). In that manner (4R)-[N'-methyl-N'-(3,5-bistrifluoromethyl-benzoyl)-amino]-4-(4-chlorobenzyl)-but-2-enoic acid N-[(R)-epsilon-caprolactam-3-yl]-amide [$R_f$0.12, ethyl acetate, $R_t$=20.38 min. (Chiracel-OJ, 0.46×25 cm, detection 210 nm, hexane:ethanol=90:10+0.1% TFA, flow rate 1.0 m/min., 30 bar)] and (4S)-[N'-methyl-N'-(3,5-bistrifluoromethyl-benzoyl)-amino]-4-(4-chlorobenzyl)-but-2-enoic acid N-[(R)-epsilon-caprolactam-3-yl]-amide [$R_f$=0.09, ethyl acetate, $R_t$=23.6 min. (Chiracel-OJ, 0.46×25 cm, detection 210 nm, hexane:isopropanol=80:20 +0.1% TFA, flow rate 1.0 ml/min., 30 bar)]are obtained in pure form.

EXAMPLE 22

Analogously to the preparation of the compounds described in Example 21, it is also possible to prepare (4R)-4-[N'-methyl-N'-(3.5-bistrifluoromethyl-benzoyl)-amino]-4-(3.4-dichlorobenzyl)-but-2-enoic acid N-[(R)-epsilon-caprolactam-3-yl]-amide The title compound is prepared starting from racemic 3,4-dichlorophenylalanine methyl ester. Racemic 3,4-dichlorophenylalanine methyl ester is reacted in a manner analogous to that described in Example 12[12g)]. In Step b), D-3-amino-epsilon-caprolactam is used, as in Step 12b). The mixture of diastereoisomers formed is then separated in a final step by chromatography on silica gel (ethyl acetate). In that manner (4R)-4-[N'-methyl-N'-(3,5-bis-trifluoromethyl-benzoyl)-amino]-4-(3,4-dichlorobenzyl)-but-2-enoic acid N-[(R)-epsilon-caprolactam-3-yl]-amide, $R_f$320.12, ethyl acetate, m.p. 115–120°, $[\alpha]_D^{2}2=+39.4°(c=0.97, ethanol)$; and (4S)-4-[N'-methyl-N'-(3,5-bistrifluoromethyl-benzoyl)-amino]-4-(3,4-dichlorobenzyl)-but-2-enoic acid N-[(R)-epsilon-caprolactam-3-yl]-amide, $R_f$=0.09, ethyl acetate, are obtained in pure form.

Analogously to the procedure described under Examples 21 and 22, it is also possible, starting from the appropriately halogenated phenylalanine derivatives, to prepare the following substances.

EXAMPLE 22A (4R)- and (4S)-4-[N'-Methyl-N'-(3,5-bistrifluoromethyl-benzoyl)-amino]-4-(3-fluoro-4-chlorobenzyl)-but-2-enoic acid N-[(R)-epsilon-caprolactam-3-yl]-amide 1st diastereoisomer: $R_f$=0.24 (ethyl acetate), and 2nd diastereoisomer: $R_f$=0.28 (ethyl acetate).

EXAMPLE 22B (4R)- and (4S)-4-[N'-Methyl-N'-(3,5-bistrifluoromethyl-benzoyl)-amino]-4-(3,4-difluorobenzyl)-but-2-enoic acid N-[(R)-epsilon-caprolactam-3-yl]-amide 1st diastereoisomer: $R_f$=0.4 (ethyl acetate:acetone=1:1), and 2nd diastereoisomer: $R_f$=0.34 (ethyl acetate:acetone=1:1).

EXAMPLE 22C (4R)- and (4S)-4-[N'-Methyl-N'-(3,5-bistrifluoromethyl-benzoyl)-amino]-4-(3,4-dibromobenzyl)-but-2-enoic acid N-[(R)-epsilon-caprolactam-3-yl]-amide 1st diastereoisomer: $R_f$=0.17 (ethyl acetate), and 2nd diastereoisomer: $R_f$=0.11 (ethyl acetate).

EXAMPLE 22D (4R)- and (4S)-4-[N'-Methyl-N'-(3,5-bistrifluoromethyl-benzoyl)-amino]-4-(3,4,5-trifluorobenzyl)-but-2-enoic acid N-[(R)-epsilon-caprolactam-3-yl]-amide 1st diastereoisomer: $R_f$=0.11 (ethyl acetate), and 2nd diastereoisomer: $R_f$=0.076 (ethyl acetate).

EXAMPLE 22E (4R)- and (4S)-4-[N'-Methyl-N'-(3.5-bistrifluoromethyl-benzoyl)-amino]-4-(4-fluorobenzyl)-but-2-enoic acid N-[(R)-epsilon-caprolactam-3-yl]-amide 1st diastereoisomer $R_f$=0.175 (ethyl acetate), and 2nd diastereoisomer: $R_f$=0.14 (ethyl acetate).

EXAMPLE 23

(4R)- or (4S)-[N'-(3,5-Bistrifluoromethyl-benzoyl)-N'-methyl-amino]-5,5-diphenyl-pent-2-enoic acid N-[(S)-epsilon-caprolactam-3-yl]-amide [is presumed to be the (4R)-derivative]

58 mg (0.47 mmol) of 4-dimethylaminopyridine (DMAP), 85 mg (0.44 mmol) of N-(3-dimethylaminopropyl)-N'-ethyl-carbodiimide hydrochloride (EDC.HCl) and 58 mg (0.44 mmol) of (S)-3-amino-hexahydro-2-azepinone are added in succession to a suspension of 207 mg (0.40 mmol) of (4R)- or (4S)-[N-(3,5-bistrifluoromethyl-benzoyl)-N-methyl-amino]-5,5-diphenyl-pent-2-enoic acid in 5 ml of methylene chloride. After being stirred at room temperature for 16 hours, the mixture is concentrated by evaporation and the residue is chromatographed on silica gel using methylene chloride/methanol (95:5). The title compound is obtained in the form of a cream-coloured solid. TLC: methylene chloride/methanol (95:5) $R_f$=0.32; ESI(+)-MS (M+H)$^+$=632; $[\alpha]_D^{20}$=+41.9°(c=1, methanol).

The starting compound is prepared as follows:

(a) 2-(N-tert-Butoxycarbonyl-N-methyl-amino)-3,3-diphenyl-propanoic acid methyl ester To a solution of 34.2 g (0.10 mol) of 2-tert-butoxycarbonylamino-3,3-diphenyl-propanoic acid (J. Med. Chem. 35, 3364, 1992) in 250 ml of N,N-dimethylformamide there are added in succession 121.9 g (0.52 mol) of silver(I) oxide in one portion and 26 ml (0.41 mol) of methyl iodide dropwise over a period of 20 minutes. After being stirred at room temperature for 26 hours the mixture is diluted with ethyl acetate; the oxide is filtered off over Hyflo and then washed with ethyl acetate. The organic phase is concentrated by evaporation first using a rotary evaporator and then under a high vacuum. The residue is dissolved in ethyl acetate, washed three times with water and once with brine, dried over sodium sulfate and concentrated by evaporation. The title compound is obtained in the form of a beige solid. TLC: methylene chloride/methanol (95:5) $R_f$=0.28; FAB-MS (M+H)$^+$=370.

(b) (1-Hydroxymethyl-2,2-diphenyl-ethyl)-methyl-carbamic acid tert-butyl ester To a solution of 32.0 g (86.6 mmol) of 2-(N-tert-butoxycarbonyl-N-methyl-amino)-3,3-diphenyl-propanoic acid methyl ester in 400 ml of ether there are added in succession 3.0 g (130.0 mmol) of lithium borohydride in portions and 5.3 ml (130 mmol) of methanol dropwise (foams!). The reaction mixture is stirred under reflux for 3 hours, then cooled in an ice bath, and 40 ml of 0.5N hydrochloric acid are added (foams!). After further dilution with water, the mixture is extracted twice with methylene chloride. The combined organic phases are dried over sodium sulfate and concentrated by evaporation, yielding the title compound in the form of a white foam. TLC: methylene chloride/methanol (95:5) $R_f$=0.46; FAB-MS (M+H)$^+$=342.

(c) (1-Formyl-2,2-diphenyl-ethyl)-methyl-carbamic acid tert-butyl ester 17.8 ml (127 mmol) of triethylamine and a solution of 22.8 g (127 mmol) of sulfur trioxide pyridine complex in 100 ml of dimethyl sulfoxide are added in succession to a solution of 14.5 g (42.5 mmol) of (1-hydroxymethyl-2,2-diphenyl-ethyl)-methyl-carbamic acid tert-butyl ester in 80 ml of dimethyl sulfoxide. After 45 minutes the reaction mixture is poured into ice-water and exhaustively extracted with ether. The combined organic phases are washed twice with 1M potassium hydrogen sulfate, twice with water and once with 1M sodium hydrogen carbonate, dried over sodium sulfate and concentrated by evaporation, yielding the title compound in the form of a yellow oil. TLC: methylene chloride/methanol (95:5) $R_f$=0.88.

(d) 4-(N-tert-Butoxycarbonyl-N-methyl-amino)-5,5-diphenyl-pent-2-enoic acid ethyl ester A solution of 14 ml (68 mmol) of phosphonoacetic acid triethyl ester in 130 ml of tetrahydrofuran is added at 0C to a solution of 3.7 g (84 mmol) of 55–65% sodium hydride dispersion (washed three times with pentane) in 130 ml of tetrahydrofuran. After 1 hour a solution of 13.6 g (40 mmol) of (1-formyl-2,2-diphenyl-ethyl)-methyl-carbamic acid tert-butyl ester in 130 ml of tetrahydrofuran is added dropwise thereto. After 4 hours the reaction mixture is rendered neutral with 1M potassium hydrogen sulfate and then diluted with water and ethyl acetate. The organic phase is washed three times with water, dried over magnesium sulfate and concentrated by evaporation. The residue is chromatographed on silica gel using methylene chloride/methanol (99:1 to 98:2). The title compound is obtained in the form of a yellow oil. TLC: methylene chloride/methanol (98:2) $R_f$=0.45.

(e) 4-Methylamino-5,5-diphenyl-Dent-2-enoic acid ethyl ester 22 ml (0.28 mol) of trifluoroacetic acid are added dropwise to a solution of 14.2 g (34.7 mmol) of 4-(tert-butoxycarbonylmethyl-amino)-5,5-diphenyl-pent-2-enoic acid ethyl ester in 100 ml of methylene chloride. After 5 hours the reaction mixture is concentrated by evaporation, and then toluene is added twice and the mixture is concentrated by evaporation. The residue is dissolved in methylene chloride, washed with saturated sodium hydrogen carbonate solution, dried over sodium sulfate and again concentrated by evaporation. The title compound is obtained in the form of a yellow oil. TLC: methylene chloride/methanol (95:5) $R_f$=0.26.

(f) 4-[N-(3,5-Bistrifluoromethyl-benzoyl)-N-methyl-amino]-5,5-diphenyl-pent-2-enoic acid ethyl ester A solution of 10.6 g (34.3 mmol) of 4-methylamino-5,5-diphenyl-pent-2-enoic acid ethyl ester in 110 ml of methylene chloride is added at 0° C. via a cannula to a solution of 6.7 ml (36.0 mmol) of 3,5-bistrifluoromethyl-benzoyl chloride in 110 ml of methylene chloride. Then 5.8 ml (41.1 mmol) of triethylamine and 0.4 g (3.4 mmol) of 4-dimethylamino- pyridine are added. After 1 hour the reaction mixture is diluted with ethyl acetate and washed twice with water and once with brine. The aqueous phases are back-extracted once with ethyl acetate. The combined organic phases are then dried over magnesium sulfate and concentrated by evaporation. The residue is chromatographed on silica gel using methylene chloride/methanol (100:0 to 98:2). The title compound is obtained in the form of a light-yellow foam. TLC: methylene chloride/methanol (98:2) $R_f$=0.38; FAB-MS (M+H)$^+$=550.

(g) (4R)- and (4S)-[N-(3,5-Bistrifluoromethyl-benzoyl)-N-methyl-amino]-5,5-diphenyl-pent-2-enoic acid ethyl ester 4.38 g (7.95 mmol) of 4-[N-(3,5-bistrifluoromethyl-benzoyl)-N-methyl-amino]-5,5-diphenyl-pent-2-enoic acid ethyl ester are chromatographed on a Chiralcel® OD-prep. column using hexane/isopropanol (99:1). The separated title compounds are obtained in the form of light-yellow foams. HPLC (Chiralcel® OD- 250×4.6 mm): hexane/isopropanol (980:20) $R_t$ (enantiomer 1)=5.28 min., $R_t$ (enantiomer 2)=7.57 min.

(h) (4R)- or (4S)-[N-(3,5-Bistrifluoromethyl-benzoyl)-N-methyl-amino]-5,5-diphenyl-pent-2-enoic acid 6.7 ml of 1N sodium hydroxide are added to a solution of 2.16 g (3.93 mmol) of (4R)- or (4S)-[N-(3,5-bistrifluoromethyl-benzoyl)-N-methyl-amino]-5,5-diphenyl-pent-2-enoic acid ethyl ester (enantiomer 2) in 30 ml of tetrahydrofuran/methanol (2:1). After 4 hours the reaction mixture is concentrated by evaporation, diluted with water and rendered acidic with cold 2N hydrochloric acid. The white precipitate is filtered off, washed with water and dried under a high vacuum at 60° C. The title compound is obtained in the form of a white solid. TLC: methylene chloride/methanol (95:5) $R_f$=0.22; ESI(-)-MS (M-H)=5°; $[\alpha]_D^2$=+38.5° (c=1, methanol).

In an analogous manner [starting from (4S)- or (4R)-[N-(3,5-bistrifluoromethyl-benzoyl)-N-methyl-amino]-5,5-diphenyl-pent-2-enoic acid, prepared from enantiomer 1 of example 23(g)] it is possible to prepare: (4S)- or (4R)-[N'-(3.5-bistrifluoromethyl-benzoyl)-N'-methyl-amino]-5,5-diphenyl-pent-2-enoic acid N-[(S)-epsilon-caprolactam-3-yl]-amide [is presumed to be the (4S)-derivative]; TLC: methylene chloride/methanol (95:5) $R_f$=0.36; ESI(+)-MS (M+H)$^+$=632; $[\alpha]_D^{20}$=−31.2°(c=1, methanol).

Examples A to E: Pharmaceutical Compositions

Example A: Tablets, each Comprising 50 mg of Active Ingredient

| Composition (10000 tablets) | |
| --- | --- |
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of the potato starch, and the mixture is moistened with an ethanolic solution of the gelatin and granulated through a sieve. After drying, the remainder of the potato starch, the magnesium stearate, the talc and the silicon dioxide are mixed in and the mixture is compressed to form tablets each weigh- ing 145 mg and comprising 50 mg of active ingredient; if desired the tablets may be provided with dividing notches for finer adaptation of the dose.

Example B: Film-coated Tablets, each Comprising 100 mg of Active Ingredient

| Composition (1000 film-coated tablets) | |
| --- | --- |
| active ingredient | 100.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| dichloromethane | q.s. |

The active ingredient, the lactose and 40 g of the corn starch are mixed together and the mixture is moistened with a paste prepared from 15 g of corn starch and water (with heating), and granulated. The granules are dried and the remainder of the corn starch, the talc and the calcium stearate are mixed with the granules. The mixture is compressed to form tablets (weight: each 280 mg) which are then film-coated with a solution of the hydroxypropylmethylcellulose and the shellac in dichloromethane (final weight of each film-coated tablet: 283 mg).

Example C: Hard Gelatin Capsules, each Comprising 100 mg of Active Ingredient

| Composition (1000 capsules) | |
| --- | --- |
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added through a sieve of 0.2 mm mesh size to the lyophilised active ingredient. The two components are intimately mixed. Then first the lactose is added through a sieve of 0.6 mm mesh size and then the microcrystalline cellulose is added through a sieve of 0.9 mm mesh size. All four components are then intimately mixed for 10 minutes. Finally, the magnesium stearate is added through a sieve of 0.8 mm mesh size. After further mixing (3 minutes), 390 mg portions of the resulting formulation are introduced into size 0 hard gelatin capsules.

Example D: An Injection or Infusion Solution, Comprising 5 mg of Active Ingredient per 2.5 ml Ampoule

| Composition (1000 ampoules) | |
| --- | --- |
| active ingredient | 5.0 g |
| sodium chloride | 22.5 g |
| phosphate buffer solution (pH: 7.4) | 300.0 g |
| demineralised water | ad 2500.0 ml |

The active ingredient and the sodium chloride are dissolved in 1000 ml of demineralised water and the solution is filtered through a microfilter. The phosphate buffer solution is added to the filtrate and the mixture is made up to 2500 ml with demineralised water. For the preparation of unit dose forms, 2.5 ml portions of the mixture are introduced into glass ampoules which then each comprise 5 mg of active ingredient.

Example E: An Inhalation Suspension, Comprising Propellant and Forming a Solid Aerosol, that Comprises 0.1% by Weight Active Ingredient

| Composition | % by weight |
| --- | --- |
| active ingredient, micronised | 0.1 |
| sorbitan trioleate | 0.5 |
| propellant A (trichlorotrifluoroethane) | 4.4 |
| propellant B (dichlorodifluoromethane and | 15.0 |
| 1,2-dichlorotetrafluoroethane) | 80.0 |

With the exclusion of moisture, the active ingredient is suspended in trichlorotrifluoroethane, with the addition of the sorbitan trioleate, using a conventional homogeniser and the suspension is introduced into an aerosol container equipped with a metering valve. The container is closed and filled up with propellant B under pressure.

What is claimed is:
1. A compound of formula I

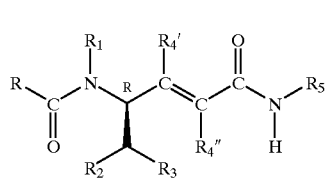

(I)

wherein
R is phenyl that is unsubstituted or is substituted by 1, 2 or 3 substituents selected from the group halogen, lower alkyl, trifluoromethyl, hydroxy and lower alkoxy,
$R_1$ is hydrogen or lower alkyl,
$R_2$ is hydrogen, lower alkyl or phenyl that is unsubstituted or is substituted by 1, 2 or 3 substituents selected from the group halogen, lower alkyl, trifluoromethyl, hydroxy and lower alkoxy, $R_3$ is phenyl that is unsubstituted or is substituted by 1, 2 or 3 substituents selected from the group halogen, lower alkyl, trifluoromethyl, hydroxy and lower alkoxy; or is naphthyl, 1H-indol-3-yl or 1-lower alkyl-indol-3-yl, $R_4'$ and $R_4''$ are each independently of the other hydrogen or lower alkyl, at least one of the radicals $R_4'$ and $R_4''$ being hydrogen, and $R_5$ is $C_3$–$C_8$cycloalkyl, D-azacycloheptan-2-on-3-yl or L-azacycloheptan-2-on-3-yl;

or a salt thereof.

2. A compound of formula I according to claim 1, wherein R is phenyl, 3,5-bistrifluoromethyl-phenyl or 3,4,5-trimethoxyphenyl, $R_1$ is hydrogen or lower alkyl, $R_2$ is hydrogen or phenyl, $R_3$ is phenyl, halo-phenyl, dihalo-phenyl, trihalo-phenyl, 2-naphthyl, 1H-indol-3-yl or 1-lower alkyl-indol-3-yl, $R_4'$ and $R_4''$ are each independently of the other hydrogen or lower alkyl, at least one of the radicals $R_4'$ and $R_4''$ being hydrogen, and $R_5$ is $C_5$–$C_7$cycloalkyl, D-azacycloheptan-2-on-3-yl or L-azacycloheptan-2-on-3-yl;

or a salt thereof.

3. A compound of formula I according to claim 1, wherein R is phenyl, 3,5-bistrifluoromethyl-phenyl or 3,4,5-trimethoxyphenyl, $R_1$ is hydrogen or lower alkyl, $R_2$ is hydrogen or phenyl, $R_3$ is phenyl, halo-phenyl, dihalo-phenyl, 2-naphthyl, 1H-indol-3-yl or 1-lower alkyl-indol-3-yl, $R_4'$ and $R_4''$ are each independently of the other hydrogen or lower alkyl, at least one of the radicals $R_4'$ and $R_4''$ being hydrogen, and $R_5$ is $C_5$–$C_7$cycloalkyl, D-azacycloheptan-2-on-3-yl or L-azacycloheptan-2-on-3-yl;

or a salt thereof.

4. A compound of formula I according to claim 1, wherein R is 3,5-bistrifluoromethyl-phenyl, $R_1$ is hydrogen, methyl or ethyl, $R_2$ is hydrogen or phenyl, $R_3$ is phenyl, 4-chlorophenyl, 4-fluorophenyl, 3,4-dichloro-phenyl, 3,4-difluoro-phenyl, 3-fluoro-4-chloro-phenyl, 3,4,5-trifluoro-phenyl, 2-naphthyl, 1H-indol-3-yl or 1-methyl-indol-3-yl, $R_4'$ and $R_4''$ are each independently of the other hydrogen or methyl, at least one of the radicals $R_4'$ and $R_4''$ being hydrogen, and $R_5$ is cyclohexyl, D-azacycloheptan-2-on-3-yl or L-azacycloheptan-2-on-3-yl;

or a pharmaceutically acceptable salt thereof.

5. A compound of formula I according to claim 1, wherein R is 3,5-bistrifluoromethyl-phenyl, $R_1$ is hydrogen, methyl or ethyl, $R_2$ is hydrogen or phenyl, $R_3$ is phenyl, 4-chlorophenyl, 4-fluorophenyl, 3,4-dichloro-phenyl, 3,4-difluoro-phenyl, 2-naphthyl, 1H-indol-3-yl or 1-methyl-indol-3-yl, $R_4'$ and $R_4''$ are each independently of the other hydrogen or methyl, at least one of the radicals $R_4'$ and $R_4''$ being hydrogen, and $R_5$ is cyclohexyl, D-azacycloheptan-2-on-3-yl or L-azacycloheptan-2-on-3-yl;

or a pharmaceutically acceptable salt thereof.

6. A compound of formula I according to claim 1, wherein R is 3,5-bistrifluoromethyl-phenyl, $R_1$ is hydrogen or methyl, $R_2$ is hydrogen or phenyl, $R_3$ is phenyl, 4-chlorophenyl, 3,4-dichloro-phenyl, 2-naphthyl, 1H-indol-3-yl or 1-methyl-indol-3-yl, $R_4'$ and $R_4''$ are hydrogen, and $R_5$ is cyclohexyl, D-azacycloheptan-2-on-3-yl or L-azacycloheptan-2-on-3-yl;

or a pharmaceutically acceptable salt thereof.

7. (4R)-[N'-Methyl-N'-(3,5-bistrifluoromethyl-benzoyl)-amino]-5-(1-methyl-indol-3-yl)-pent-2-enoic acid N-[(R)-epsilon-caprolactam-3-yl]-amide according to claim 1.

8. (4R)-[N'-Methyl-N'-(3,5-bistrifluoromethyl-benzoyl)-amino]-5-(1-methyl-indol-3-yl)-pent-2-enoic acid N-[(S)-epsilon-caprolactam-3-yl]-amide according to claim 1.

9. (4R)-[N'-Methyl-N'-(3,5-bistrifluoromethyl-benzoyl)-amino]-4-(4-chlorobenzyl)-but-2-enoic acid N-[(R)-epsilon-caprolactam-3-yl]-amide according to claim 1.

10. (4R)-4-[N'-Methyl-N'-(3,5-bistrifluoromethyl-benzoyl)-amino]-4-(3,4-dichlorobenzyl)-but-2-enoic acid N-[(R)-epsilon-caprolactam-3-yl]-amide according to claim 1.

11. A pharmaceutical composition comprising a compound according to claim 1 and at least one pharmaceutically acceptable carrier.

12. A process for the preparation of a compound of formula I according to claim 1, which process comprises (A) N-acylating a compound of formula II

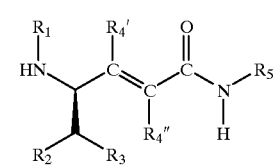

(II)

with a carboxylic acid R—C(=O)—OH, or with a reactive derivative thereof, or (B) condensing a carboxylic acid of formula III

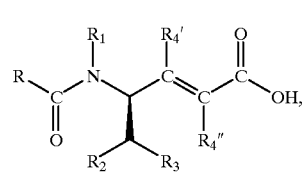

(III)

or a reactive derivative thereof, with a $C_3$–$C_8$cycloalkylamine or D(+)- or L(−)-3-amino-epsilon-caprolactam, or (C) as a last step, synthesising the double bond by a Wittig reaction or a variant thereof, for example Wittig-Horner;

and, if desired, converting a compound of formula I into a different compound of formula I and/or, if desired, converting a resulting salt into the free compound or into a different salt and/or, if desired, converting a resulting free compound of formula I having salt-forming properties into a salt and/or, if desired, separating a resulting mixture of stereoisomers, diastereoisomers or enantiomers into the individual stereoisomers, diastereoisomers or enantiomers.

13. A method of treatment of diseases responsive to antagonization of the NK1 receptor and/or NK2 receptor comprising administering to a patent in need of such treatment an effective amount of a compound of formula I according to claim 1.

14. A method of treating and/or inhibiting neurogenic inflammation and tachykinin bronchoconstriction comprising administering to a patient in need of such treating and/or inhibiting an effective amount of a compound of formula I according to claim 1.

* * * * *